(12) United States Patent
Gillam et al.

(10) Patent No.: US 8,671,066 B2
(45) Date of Patent: Mar. 11, 2014

(54) MEDICAL DATA PREDICTION METHOD USING GENETIC ALGORITHMS

(75) Inventors: Michael Gillam, Redmond, WA (US); Renato R. Cazangi, Redmond, WA (US); Alexey P. Kontsevoy, Redmond, WA (US); Uri Kartoun, Redmond, WA (US)

(73) Assignee: Microsoft Corporation, Redmond, WA (US)

( * ) Notice: Subject to any disclaimer, the term of this patent is extended or adjusted under 35 U.S.C. 154(b) by 419 days.

(21) Appl. No.: 12/981,888

(22) Filed: Dec. 30, 2010

(65) Prior Publication Data

US 2012/0173468 A1    Jul. 5, 2012

(51) Int. Cl.
*G06F 15/18* (2006.01)
*G06N 3/12* (2006.01)

(52) U.S. Cl.
USPC .......................................................... 706/13

(58) Field of Classification Search
None
See application file for complete search history.

(56) References Cited

U.S. PATENT DOCUMENTS

| | | | |
|---|---|---|---|
| 6,341,292 B1 | 1/2002 | Cho et al. | |
| 6,606,615 B1 | 8/2003 | Jennings et al. | |
| 7,730,063 B2 * | 6/2010 | Eder | 707/736 |
| 2003/0095151 A1 * | 5/2003 | Shackleford et al. | 345/833 |
| 2004/0249620 A1 * | 12/2004 | Chandra et al. | 703/11 |
| 2005/0149459 A1 | 7/2005 | Kofman et al. | |
| 2007/0078950 A1 | 4/2007 | Hopkins et al. | |
| 2008/0097942 A1 * | 4/2008 | Zhao et al. | 706/13 |
| 2008/0270331 A1 * | 10/2008 | Taylor et al. | 706/13 |
| 2010/0179930 A1 * | 7/2010 | Teller et al. | 706/12 |

OTHER PUBLICATIONS

Leardi, Application of a Genetic Algorithm to Feature Selection Under Full Validation Conditions and to Outlier Detection, 1994.*
Microsoft Time Series Algorithm Technical Reference, SQL Server 2008 R2.*
Lameijer et al, The Molecule Evoluator. An Interactive Evolutionary Algorithm for the Design of Drug-Like Molecules, 2006.*
Baumann, Cross-validation as the objective function for variable-selection techniques, 2003.*
Szpiro, Forecasting chaotic time series with genetic algorithms.*
Dowsland et al, A simulated annealing based hyperheuristic for determining shipper sizes for storage and transportation, 2005.*
Tarantilis et al, A threshold accepting metaheuristic for the heterogeneous fixed fleet vehicle routing problem, 2004.*
Rudolph et al, A Cellular Genetic Algorithm with Self-Adjusting Acceptance Threshold, 1995.*
"Quantification of Health Commodities—A Guide to Forecasting and Supply Planning for Procurement", Retrieved at << http://deliver.jsi.com/dlvr_content/resources/allpubs/guidelines/QuantHealthComm.pdf >>, Mar. 2009, pp. 56.
Yurkiewicz, Jack., "Forecasting 2000", Retrieved at << http://lionhrtpub.com/orms/orms-2-00/forecast.html >>, Feb. 2000, pp. 5.

(Continued)

*Primary Examiner* — Jeffrey A Gaffin
*Assistant Examiner* — Mikayla Chubb
(74) *Attorney, Agent, or Firm* — Damon Rieth; Jim Ross; Micky Minhas

(57) ABSTRACT

A method may use a genetic algorithm to varying prediction parameters in forecasting software to obtain optimal predictions is disclosed. The method identifies parameters that can be varied and by modifying the parameters, the predictions of the forecasting software improve. The method uses sample data to train and validate the forecast and the optimal forecasting parameters are determined.

20 Claims, 4 Drawing Sheets

(56) References Cited

OTHER PUBLICATIONS

Newberne, Captain Joan H., "Holt-Winters Forecasting: A Study of Practical Applications for Healthcare Managers", Retrieved at << http://www.dtic.mil/cgi-bin/GetTRDoc?AD=ADA473648&Location=U2&doc=GetTRDoc.pdf>>, May 25, 2006, pp. 37.

Chang, et al., "The development of a weighted evolving fuzzy neural network for PCB sales forecasting", Retrieved at << http://citeseerx.ist.psu.edu/viewdoc/download?doi=10.1.1.97.6876&rep=rep1&type=pdf >>, Expert Systems with Applications 32 (2007), pp. 86-96.

Werner, et al., "The development of a weighted evolving fuzzy neural network for PCB sales forecasting", Retrieved at << http://citeseerx.ist.psu.edu/viewdoc/download?doi=10.1.1.97.6876&rep=rep1&type=pdf >>, Proceedings 6th European Conference, Apr. 14-16, 2003, pp. 10.

\* cited by examiner

US 8,671,066 B2

MEDICAL DATA PREDICTION METHOD USING GENETIC ALGORITHMS

BACKGROUND

Making predictions has long been a pursuit of mankind. Logically, over time, prediction methods have improved. As prediction methods have improved, more fields of endeavors have become interested in using modern prediction tools to assist with their work. However, modern prediction tools while becoming more accurate have become increasingly difficult to use and understand by virtually anyone aside from dedicated, full time prediction software experts. This has severely limited the ability to use and take full advantage of modern statistical prediction software, including using the software in medical forecasting uses.

SUMMARY

A genetic algorithm method to varying prediction parameters in forecasting software to obtain optimal predictions is disclosed. Forecasting algorithms have parameters that need to be adjusted to influence the results. The genetic algorithm adjusts the parameters and optimizes them to try to cause better results to emerge. The method identifies parameters that can be varied and by modifying the parameters, the predictions of the forecasting software change. During the modification of the parameters, real-time displays of the progress of the predictions are displayed. The method uses sample data to train and validate the forecast and to determine the optimal forecasting parameters.

The method has several embodiments and in one embodiment, numerous prediction parameters are created at random. The prediction parameters are mutated and the prediction accuracy is assessed. If the accuracy is sufficient, the method may stop. If the accuracy is not sufficient, the prediction parameters are modified through a variety of ways and modified prediction parameters are created. The modified prediction parameters are then used to create predictions and the accuracy is again accessed until the accuracy hits a threshold or the method has executed for a sufficient number of times or until the accuracy is sufficient or the user decides to stop the process arbitrarily.

SPECIFICATION

Figure 1:
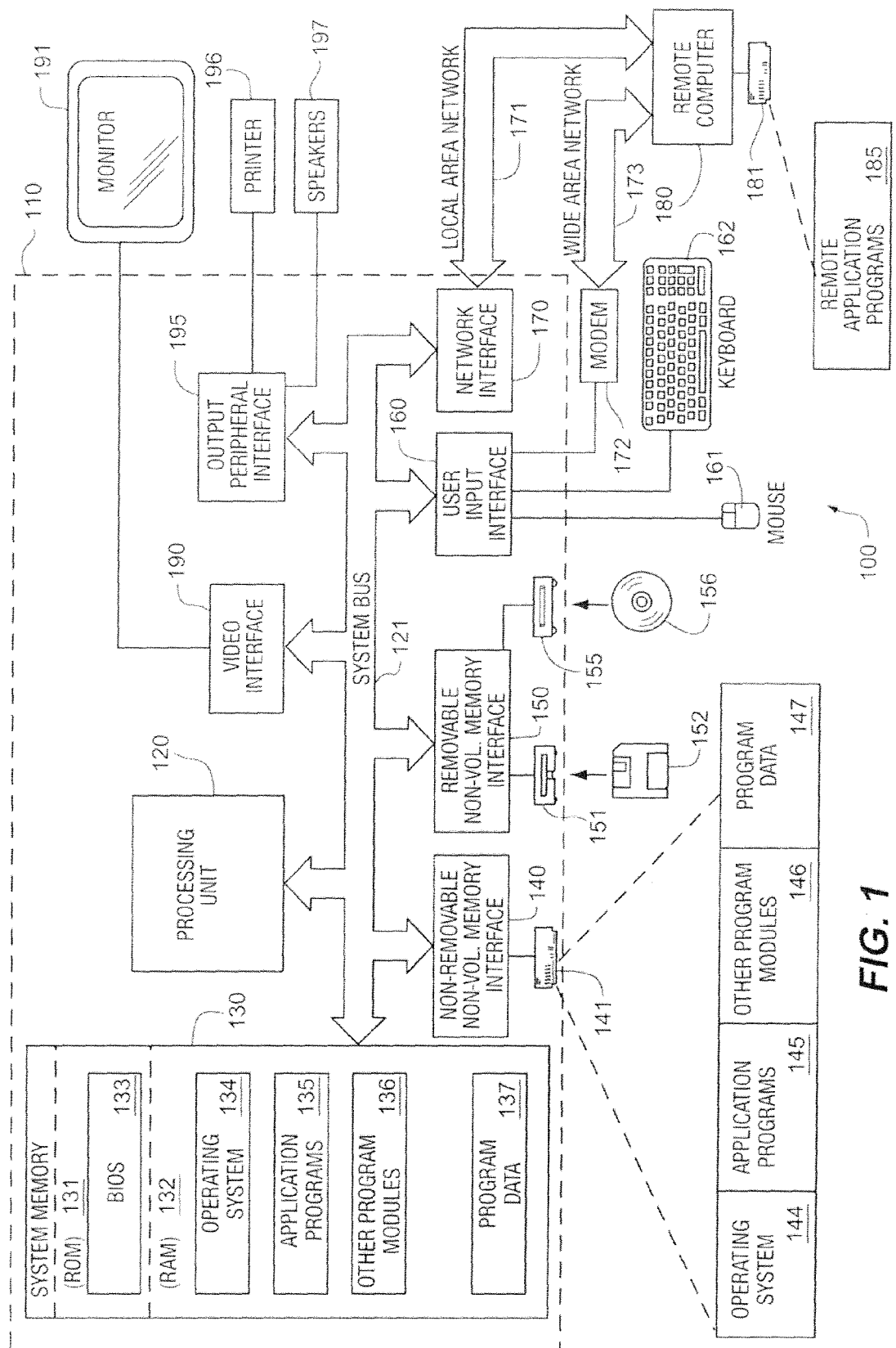
FIG. 1 illustrates a sample computing device that may be physically configured according to computer executable instructions.

FIG. 1 illustrates an example of a suitable computing system environment 100 that may be physically configured to operate, display device and provide a shopper interface described by this specification. It should be noted that the computing system environment 100 is only one example of a suitable computing environment and is not intended to suggest any limitation as to the scope of use or functionality of the method and apparatus of the claims. Neither should the computing environment 100 be interpreted as having any dependency or requirement relating to any one component or combination of components illustrated in the exemplary operating environment 100. In one embodiment, the device described in the specification is entirely created out of hardware as a dedicated unit that is physically transformed according to the description of the specification and claims. In other embodiments, the device executes software and yet additional embodiment, the device is a combination of hardware that is physically transformed and software.

With reference to FIG. 1, an exemplary system that may be physically configured for implementing the blocks of the claimed method and apparatus includes a general purpose computing device in the form of a computer 110. Components of computer 110 may include, but are not limited to, a processing unit 120, a system memory 130, and a system bus 121 that couples various system components including the system memory to the processing unit 120.

The computer 110 may operate in a networked environment using logical connections to one or more remote computers, such as a remote computer 180, via a local area network (LAN) 171 and/or a wide area network (WAN) 173 via a modem 172 or other network interface 170. In addition, not all the physical components need to be located at the same place. In some embodiments, the processing unit 120 may be part of a cloud of processing units 120 or computers 110 that may be accessed through a network.

Computer 110 typically includes a variety of computer readable media that may be any available media that may be accessed by computer 110 and includes both volatile and nonvolatile media, removable and non-removable media. The system memory 130 may include computer storage media in the form of volatile and/or nonvolatile memory such as read only memory (ROM) 131 and random access memory (RAM) 132. The ROM may include a basic input/output system 133 (BIOS). RAM 132 typically contains data and/or program modules that include operating system 134, application programs 135, other program modules 136, and program data 137. The computer 110 may also include other removable/non-removable, volatile/nonvolatile computer storage media such as a hard disk drive 141 a magnetic disk drive 151 that reads from or writes to a magnetic disk 152, and an optical disk drive 155 that reads from or writes to an optical disk 156. The hard disk drive 141, 151, and 155 may interface with system bus 121 via interfaces 140, 150. However, none of the memory devices such as the computer storage media are intended to cover transitory signals or carrier waves.

A user may enter commands and information into the computer 20 through input devices such as a keyboard 162 and pointing device 161, commonly referred to as a mouse, trackball or touch pad. Other input devices (not illustrated) may include a microphone, joystick, game pad, satellite dish, scanner, or the like. These and other input devices are often connected to the processing unit 120 through a shopper input interface 160 that is coupled to the system bus, but may be connected by other interface and bus structures, such as a parallel port, game port or a universal serial bus (USB). A monitor 191 or other type of display device may also be connected to the system bus 121 via an interface, such as a video interface 190. In addition to the monitor, computers may also include other peripheral output devices such as speakers 197 and printer 196, which may be connected through an output peripheral interface 190.

In additional embodiments, the processing unit 120 may be separated into numerous separate elements that may be shut down individually to conserve power. The separate elements may be related to specific functions. For example, an electronic communication function that controls Wi-Fi, Bluetooth, etc, may be a separate physical element that may be turned off to conserve power when electronic communication is not necessary. Each physical elements may be physically configured according to the specification and claims described herein.

Figure 2:
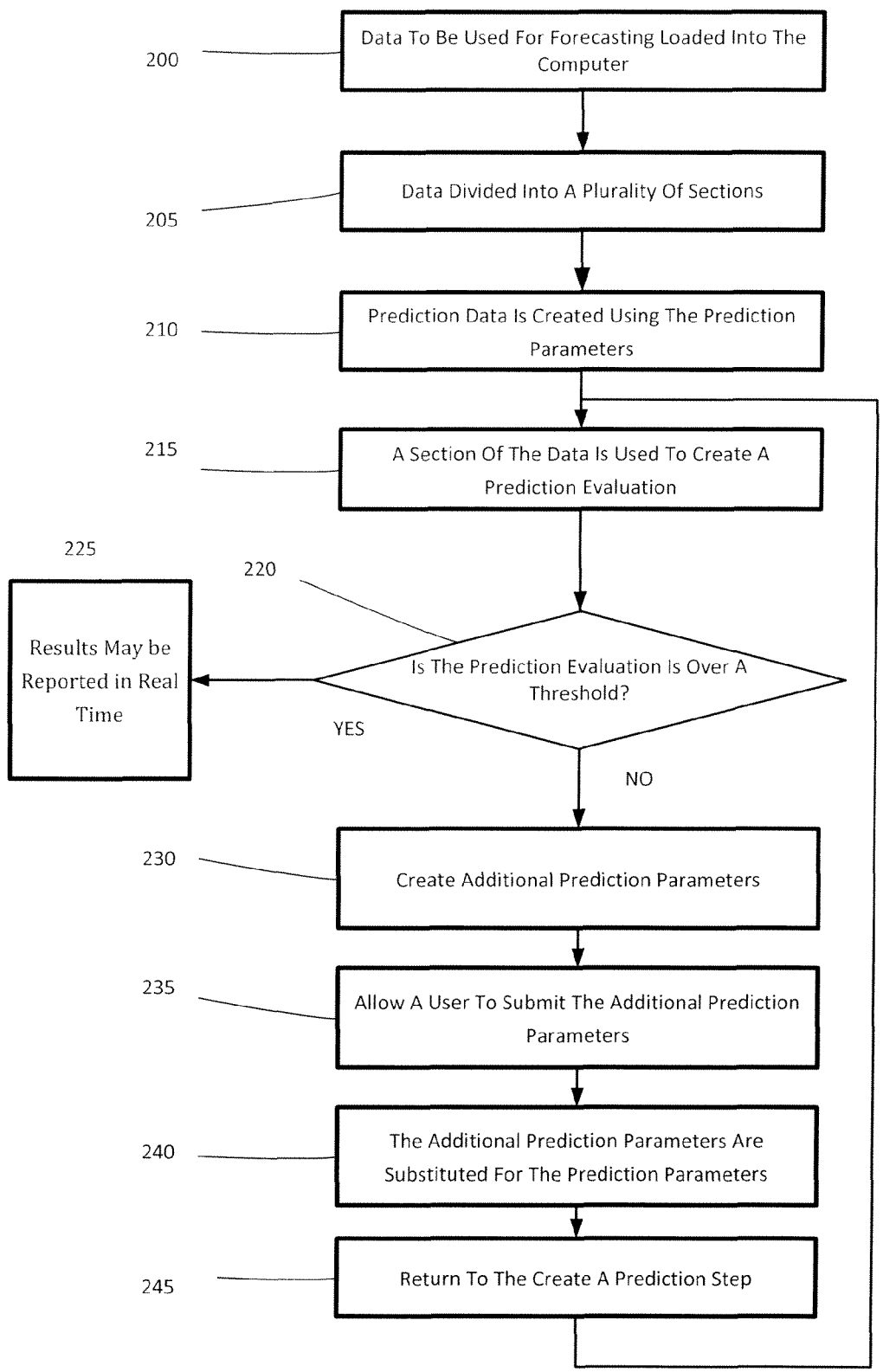
FIG. 2 illustrates steps that are executed by the physically configured computing device.

FIG. 2 illustrates a computer 110 implemented method of using genetic algorithms to create predictions of data. In some embodiments, the method is used to analyze medical related data. The medical domain is very different than other domains when prediction models are considered. One reason for that is the dependency of medical data on multiple sensing devices, operating simultaneously. As technology advances, more medical sensing devices are becoming available. Such devices allow evaluating a patient's condition more accurately. They also allow assessing the extent of large impact medical situations such as epidemics, better. Using the variety of input sensing parameters to conduct predictions on medical data may significantly improve the quality of healthcare. This is achieved by the ability of medical prediction methods such as the one described herein, to early detect the potential of a medical risk. Another ability of such methods is to early warn on the upcoming event of wide spreading diseases such influenza or malaria. The immense amount of raw data received from medical sensing devices, from multiple resources and in real-time, requires applying more sophisticated prediction methods. Possible uses may be the prediction and monitoring of cell growth and disease dispersion, muscle stimulation patterns of arm\leg movements, sleep medical signals, tumor motion, analysis and modeling of heart rate variability, prediction for improved management of glucose levels, etc. The method may be implemented on a purpose built device such a computer 110 that is transformed to execute the method or may be in software that physically configures a computing device 110 to execute the method or variations of the method. In other embodiments, the method may operate in a cloud computing environment where the application is executed in the cloud and communication between the cloud and the display occurs over a network 173. In other embodiments, the applications are spread over a variety of computing devices 110 but work together to create an integrated device or user experience. Of course, other embodiments are possible and are contemplated.

The use of predictions in the medical field is growing. The applications and hardware devices to make predictions have improved over time but so has the complexity of these applications/devices. The software and devices to make predictions are hard to use except by a few skilled forecasting professionals as the application/hardware requires adjustments to forecasting parameters that very few in the medical field understand. The claimed system/method/device attempt to use a genetic algorithm to adjust the prediction parameters to obtain an optimal solution to predicting a set of data. As a result, the prediction process may be automated in order to help doctors, nurses, etc. to have more time to spend with patient care and medical procedures.

At block 200, data to be used for forecasting may be loaded into the computer 110. As mentioned previously, the data may be medical related data. In general, most physicians are not deeply skilled at statistical analysis. The processor 120 described herein is configured to make statistical analysis as easy as clicking a button. In addition, the user or physician can watch (and interact with) the method work as displayed on a user interface such as a display 191. The method uses a genetic algorithm to adjust prediction parameters 300 (FIG. 3) used by statistical analysis software to obtain an optimal result. There are many different prediction algorithms and the algorithms may use different prediction parameters 300, but the described embodiments of the method may be applied to any of the algorithms and the related prediction parameters 300.

At a high level, a genetic algorithm is a programming technique that mimics biological evolution as a problem-solving strategy. Given a specific problem to solve, the input to the genetic algorithm is a set of potential solutions to that problem, encoded in some fashion, and a metric called a fitness function that allows each candidate to be evaluated. These candidates may be solutions already known to work, with the aim of the genetic algorithm being to improve them, but more often they are generated at random.

The genetic algorithm then evaluates each candidate according to the fitness function. In a pool of randomly generated candidates, of course, most will not work at all, and these will be discarded by natural selection or natural pressure. However, purely by chance, a few may hold promise—they may show activity, even if only weak and imperfect activity, toward solving the problem.

These promising candidates are kept and allowed to reproduce. Multiple copies are made of them, but the copies are not identical; random changes are introduced during the copying process. These digital offspring then go on to the next generation, forming anew pool of candidate solutions, and are subjected to a second round of fitness evaluation. Those candidate solutions which were worsened, or made no better, by the changes to their code are again discarded; but again, purely by chance, the random variations introduced into the population may have improved some individuals, making them into better, more complete or more efficient solutions to the problem at hand. Again these winning individuals are selected and copied over into the next generation with random changes, and the process repeats. The expectation is that the average fitness of the population will increase each round, and so by repeating this process for hundreds or thousands of rounds, very good or potentially optimal solutions to the problem can be discovered.

At block 205, the data may be divided into a plurality of sections. In one embodiment, the data may be divided into four sections being that the number of sections may be virtually any number. A first section may be used to train the model and additional sections may be used to validate the model. In one embodiment, the sections may be rotated until all the sections have both been used to train the model and to validate the model. Of course, other manners of using the data to train and validate the model are possible and are contemplated.

At block 210, prediction data 310 may be created using the prediction parameters 300. The prediction data 310 may be created by executing the prediction algorithm using the prediction parameters 300 to create prediction data 310. In one embodiment, the prediction parameters may include periodicity, complexity penalty, forecast method, historic model count, historic model gap, instability sensitivity, maximum series value, minimum series value, minimum support, missing value substitution, periodicity hint, prediction smoothing, time series length, and time series density. Of course, the prediction parameters 300 may vary depending on which of the many prediction algorithms that are used. The following are just one example and not limitation of a set of possible prediction parameters 300:

| Parameter | Description |
| --- | --- |
| AUTO_DETECT_PERIODICITY | Specifies a numeric value between 0 and 1 that detects periodicity. The default is 0.6.<br>If the value is closer to 0, periodicity is detected only for strongly periodic data.<br>Setting this value closer to 1 favors the discovery of many patterns that are almost periodic and the automatic generation of periodicity hints.<br>Note: Dealing with many periodicity hints will likely lead to significantly longer model training times, but more accurate models. |
| COMPLEXITY_PENALTY | Controls the growth of the decision tree. The default is 0.1.<br>Decreasing this value increases the chance of a split. Increasing this value decreases the chance of a split. |
| FORECAST_METHOD | Specifies which algorithm to use for analysis and prediction. Possible values are ARTXP (Auto Regression Trees with Cross Predict), ARIMA (Autoregressive Integrated Moving Average), or MIXED. The default is MIXED. |
| HISTORIC_MODEL_COUNT | Specifies the number of historic models that will be built. The default is 1. |
| HISTORICAL_MODEL_GAP | Specifies the time lag between two consecutive historic models. The default is 10. The value represents a number of time units, where the unit is defined by the model.<br>For example, setting this value to g causes historic models to be built for data that is truncated by time slices at intervals of 1*g, 2*g, etc. |
| INSTABILITY_SENSITIVITY | Controls the point at which prediction variance exceeds a certain threshold and the ARTXP (Auto Regression Trees with Cross Predict) algorithm suppresses predictions. The default value is 1.<br>The normalized standard deviation for each prediction is monitored; as soon as the standardize deviations for any prediction exceeds the threshold, the time series algorithm returns a NULL and stops the prediction process.<br>A value of 0 stops instability detection. This means that an infinite number of predictions may be created, regardless of the variance. |
| MAXIMUM_SERIES_VALUE | Specifies the maximum value to use for predictions. This parameter is used, together with MINIMUM_SERIES_VALUE, to constrain the predictions to some expected range. For example, it may be specified that the predicted data quantity for any day should never exceed the number of products in inventory. |
| MINIMUM_SERIES_VALUE | Specifies the minimum value that can be predicted. This parameter is used, together with MAXIMUM_SERIES_VALUE, to constrain the predictions to some expected range. For example, it may be specified that the predicted data quantity should never be a negative number. |
| MINIMUM_SUPPORT | Specifies the minimum number of time slices that are required to generate a split in each time series tree. The default is 10. |
| MISSING_VALUE_SUBSTITUTION | Specifies bow gaps in historical data are filled. By default, gaps in data are not allowed.<br>The following table lists the possible values for this parameter:<br>Previous—repeats the value from the previous time slice.<br>Mean—uses a moving average of time slices used in training.<br>Numeric Constant—uses the specified number to replace all missing values.<br>None—replaces missing values with values plotted along the curve of the trained model. This is the default value.<br>If the data contains multiple series, the series also cannot have ragged edges. That is, all series should have the same start and end points. |
| PERIODICITY_HINT | Provides a hint to the algorithm as to the periodicity of the data. For example, if data vary |

| Parameter | Description |
|---|---|
| | by year, and the unit of measurement in the series is months, the periodicity is 12. This parameter takes the format of {n [, n]}, where n is any positive number. The n in the brackets [ ] is optional and can be repeated as frequently as needed. For example, to provide multiple periodicity hints for data supplied monthly, {12, 3, 1} might be entered to detect patterns for the year, quarter, and month. However, periodicity has a strong effect on model quality. If the hint that is given differs from the actual periodicity, the results can be adversely affected. The default is {1}. |
| PREDICTION_SMOOTHING | Specifies how the model should be mixed to optimize forecasting. Any value between 0 and 1 may be typed or one of the following values may be used: 0—specifies that prediction uses ARTXP only. Forecasting is optimized for fewer predictions. 1—specifies that prediction uses ARIMA only. Forecasting is optimized for many predictions. 0.5 (Default)—specifies that for prediction both algorithms should be used and the results blended. |

Additional parameter examples related directly to the data and not to the forecasting algorithm can be found in the table below:

| | |
|---|---|
| TIME_SERIES_LENGTH | Specifies the time range length of the raw medical data, for example, the length may be measured in a range of seconds, minutes, days, weeks, etc. A long length does not necessarily guarantee an optimal prediction, and vice versa—a small length does not either guarantee optimal prediction, thereby, an optimal length may be determined. |
| TIME_SERIES_DENSITY | Controls the number of observations per time unit of the raw medical data, for example, a low number of observations per time unit may not be sufficient to produce accurate predictions, while a high number of observations per time unit may result a high computational cost which may produce a non-applicable prediction model, thereby, an optimal density may be determined. |

The initial set of prediction parameters 300 may be created using a random function. The prediction parameters 300 may then be adjusted over time At block 215, a section of the data may be used to create a prediction evaluation 310 where the prediction evaluation 310 indicates the accuracy of the prediction algorithm results. In one embodiment, the prediction data from the prediction algorithm is compared to actual data in the section. A statistical analysis of the prediction data in comparison to the actual data the prediction's method was attempting to predict is created. The statistical analysis may use a sum of squares error evaluation. Of course, other error evaluation methods may be acceptable.

The prediction evaluation 310 may be stored along with the prediction parameters 300 in memory 130. The prediction evaluation 310 and prediction parameters 300 may be selected that are optimal. In one embodiment, the optimal prediction parameters 300 may have the lowest "least squares sum of the differences" amount.

Figure 3:
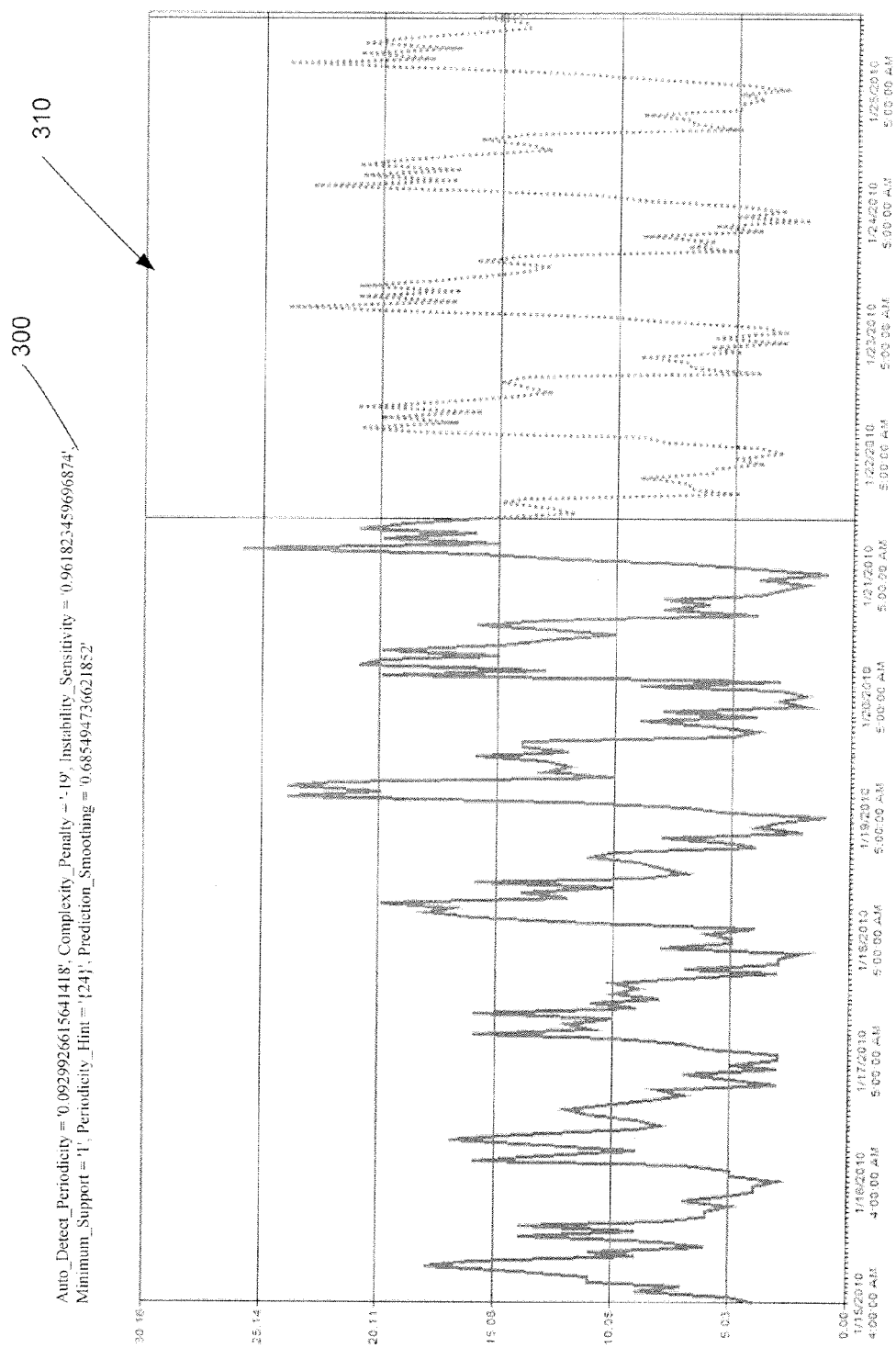
FIG. 3 illustrates a sample display image of the prediction as the method progresses to modify the prediction parameters.

The progress of the method may be displayed on a display 191 in real-time. FIG. 3 may illustrate a sample screen shot of a graph of the prediction data and a graph of the actual data. In some embodiments, the current values of all of the prediction parameters 300 are displayed in real-time wherein real-time is substantially as quickly as the predictions are created.

The progress may be displayed on a monitor 191 in communication with a computing device 110. In one embodiment, a computer 110 is physically transformed to execute the method and the display 191 is in direct communication, either through wired or wireless communication, with the computer 110. In another embodiment, the display 191 is on a portable computing device 110 such as a personal digital assistant with wireless access, a cell phone, a notebook computer, a pad type computing device, etc.

At block 220, it may be determined if the prediction evaluation 310 is above an accuracy threshold. The threshold may be pre-set or may be modified by a user. In some embodiments, the threshold may be that the prediction evaluation 310 is higher than all previous prediction evaluations 310. In other embodiments, the threshold may be set by the method by observing the results of previous evaluations and determining that significant improvements above the current prediction evaluation 310 are not probable. For example, if the prediction evaluation 310 has not improved after a statistically significant number of iterations, the threshold may be lowered and the method may end. Similarly, if the prediction evaluation 310 continues to improve after numerous iterations, the threshold may be raised until the prediction evaluation 310 slows its rate of improvement. At block 225, if the prediction evaluation 310 is above the threshold, the results may be reported in real-time. The results may be displayed on the display 191. The results may have a separate display image or may mimic the real-time reporting of the method.

At block 230, if the prediction evaluation 310 is below the threshold, additional prediction parameters 300 may be created. The additional prediction parameters 300 may be created in a variety of ways. In one embodiment, the additional prediction parameters 300 may be created by adjusting the crossover or mutation rate of the prediction parameters 300.

Hierarchical selection is one manner to sift the prediction parameters 300: Individual sets of prediction parameters 300 go through multiple rounds of selection. Lower-level evaluations may be faster and less discriminating, while those that survive to higher levels are evaluated more rigorously. The advantage of this method is that it reduces overall computation time by using faster, less selective evaluation to weed out the majority of prediction parameters 300 sets that show little or no promise, and only subjecting those who survive this initial test to more rigorous and more computationally expensive fitness evaluation. Once the selection has chosen fit prediction parameters 300, they may be randomly altered in hopes of improving their fitness for the next generation. There are two basic strategies to randomly alter the prediction parameters 300.

The first and simplest is mutation. Just as mutation in living things changes one gene to another, so mutation in a genetic algorithm causes small alterations at single points in an individual's code. In this case, prediction parameters 300 may be randomly altered.

The second method is crossover, and entails choosing two individuals to swap segments of their code, producing artificial "offspring" that are combinations of their parents. This process is intended to simulate the analogous process of recombination that occurs to chromosomes during sexual reproduction. Common forms of crossover include single-point crossover, in which a point of exchange is set at a random location in the two individuals' genomes, and one individual contributes all its code from before that point and the other contributes all its code from after that point to produce an offspring, and uniform crossover, in which the value at any given location in the offspring's genome is either the value of one parent's genome at that location or the value of the other parent's genome at that location, chosen with 50/50 probability.

Crossover and mutation. The below diagrams illustrate the effect of each of these genetic operators on individuals in a population of 8-bit strings. Each of the digits may represent a prediction parameter 300 value. The following diagram shows two individuals undergoing single-point crossover; the point of exchange is set between the fifth and sixth positions in the genome, producing a new individual that is a hybrid of its progenitors.

00101101
10110011
10110101

The following diagram shows an individual undergoing mutation position 4, changing the 0 at that position in its genome to a 1.

00101101
00111101

The encoding is not necessarily binary. It may be real, integer, custom made, a combination of different types, etc. Other ways of mutating the prediction parameters 300 also are possible. In fact, there are many different techniques which a genetic algorithm can use to select the individuals to be copied over into the next generation, but listed below are some of the most common methods. Some of these methods are mutually exclusive, but others can be and often are used in combination.

Elitist selection—the most fit members of each generation of prediction parameters 300 are guaranteed to be selected. Commonly, most genetic algorithms do not use pure elitism, but instead use a modified form where the single best, or a few of the best, individuals from each generation are copied into the next generation just in case nothing better turns up.

Fitness-proportionate selection—more fit individuals are more likely, but not certain, to be selected.

Roulette-wheel selection—a form of fitness-proportionate selection in which the chance of an individual's being selected is proportional to the amount by which its fitness is greater or less than its competitors' fitness. Conceptually, this selection may be represented as a game of roulette—each individual gets a slice of the wheel, but more fit ones may receive larger slices than less fit ones. The wheel is then spun, and whichever individual "owns" the section on which it lands each time is chosen.

Scaling selection—as the average fitness of the population increases, the strength of the selective pressure also increases and the fitness function becomes more discriminating. This method can be helpful in making the best selection later on when all individuals have relatively high fitness and only small differences in fitness distinguish one from another.

Tournament selection—subgroups of individuals are chosen from the larger population, and members of each subgroup compete against each other. Only one individual from each subgroup is chosen to reproduce.

Rank selection—each individual in the population is assigned a numerical rank based on fitness, and selection is based on this ranking rather than absolute differences in fitness. The advantage of this approach is that it can prevent very fit individuals from gaining dominance early at the expense of less fit ones, which would reduce the population's genetic diversity and might hinder attempts to find an acceptable solution.

Generational selection—the offspring of the individuals selected from each generation become the entire next generation. No individuals are retained between generations.

Steady-state selection—the offspring of the individuals selected from each generation go back into the pre-existing gene pool, replacing some of the less fit members of the previous generation. Some individuals are retained between generations.

At block 235, the user may be permitted to stop the iterations and submit the additional parameters 300. In some situations, the user may want to add input to the process. For example, the user may know that a particular adjustment may greatly speed up the process and improve the prediction. The method may be stopped and a user may be permitted to submit the additional parameters 300.

At block 240, the additional prediction parameters 300 (either from the user or generated by block 230) may be substituted for the prediction parameters 300. And, at block 245 the "create a prediction" block 215 may be repeated for a desired time or until the prediction evaluation 310 is above the threshold.

Figure 4:
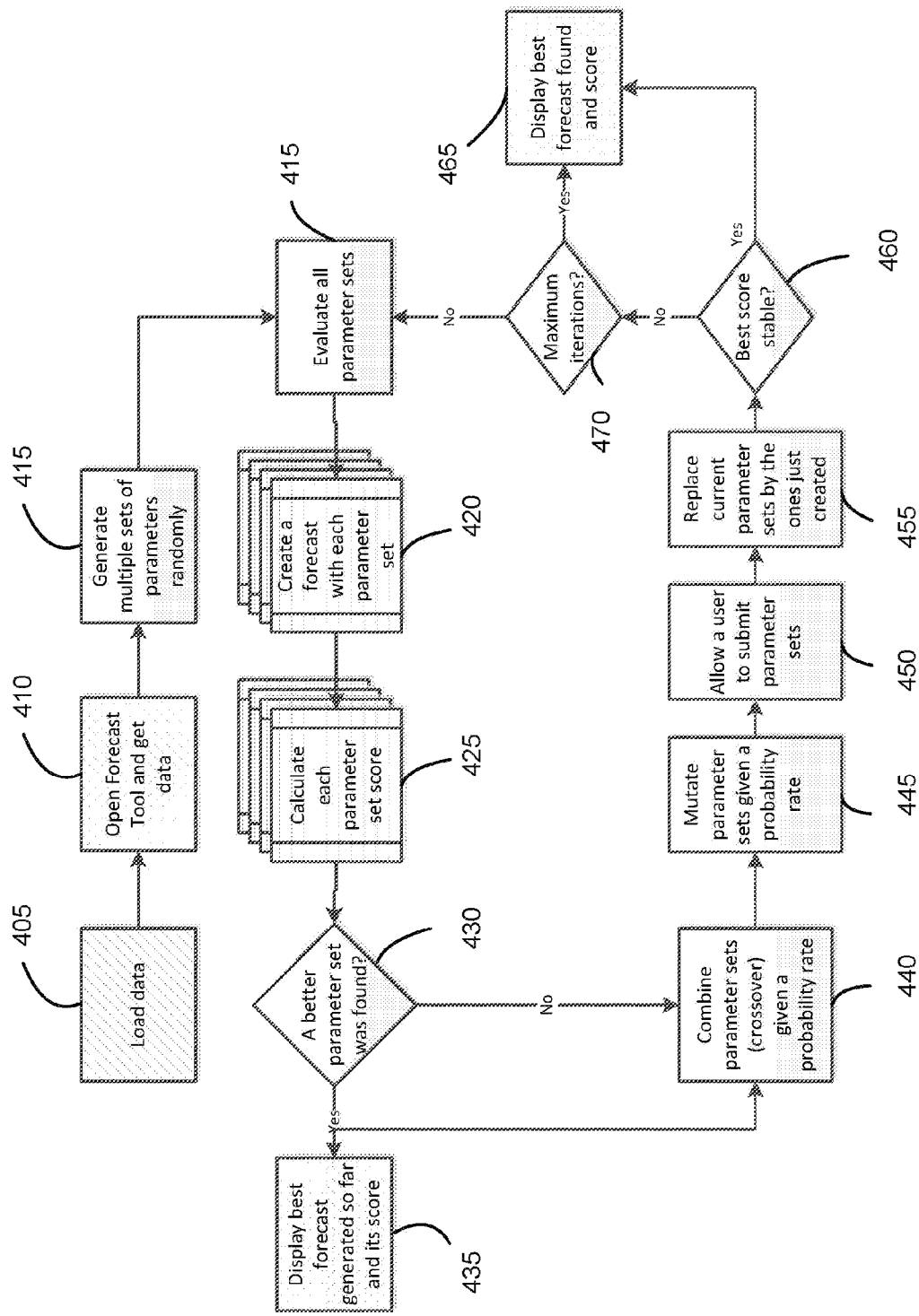
FIG. 4 illustrates steps that are executed by the physically configured computing device.

FIG. 4 illustrates another computer based method of using genetic algorithms to create predictions of data, including medical data. At block 400, data may be loaded in the computer memory such as memory 130 (FIG. 1) to be used for forecasting. The data may be from a database or may be a file of data. The file itself may be a binary file, alpha file or may be any file type. In some embodiments, a database such as Microsoft Corporation SQL® database may be used.

At block 405, a forecasting tool may be launched. As explained previously, the forecasting tool may take in data and make predictions by analyzing the data and virtually any forecasting application may work.

At block 410, multiple sets of prediction parameters 300 may be generated. In one embodiment, the prediction parameters 300 are generated randomly. In one embodiment, the prediction parameters 300 may include periodicity, complexity penalty, forecast method, historic model count, historic model gap, instability sensitivity, maximum series value, minimum series value, minimum support, missing value substitution, periodicity hint, prediction smoothing, time series length, and time series density. Of course, other embodiments are possible.

At block 415, all the prediction parameters 300 may be evaluated. As mentioned previously, there are many different prediction algorithms and the algorithms may use different prediction parameters 300, but the described embodiments of the method may be applied to any of the algorithms and the related prediction parameters 300.

At block 420, a forecast may be created by using a prediction algorithm, to create a forecast with each of the prediction parameter 300 sets. In other words, the prediction parameters 300 are used to generate value for periodicity, complexity penalty, etc., and the method generates predictions using the prediction parameters 300.

At block 425, a prediction parameter 300 set score is calculated for each prediction parameter. The parameter set score may indicate the accuracy of the prediction algorithm using the prediction parameters 300. As mentioned previously, statistical methods may be used to evaluate the accuracy of the prediction algorithm using the specific prediction parameters 300. In one embodiment, the parameter set score 310 is created using a statistical analysis of the prediction data in comparison to the actual data the prediction algorithm was attempting to predict. In some embodiments, the statistical analysis uses a sum of squares error evaluation but other methods are possible.

In one embodiment, a first section of data may be used to train the model and a second section of data to validate the model. The sections may be rotated until all the sections have both been used to train the model and to validate the model.

At block 430, it may be determined whether a better prediction parameter 300 set was found. In one embodiment, a parameter set score 310 of the prediction parameters 300 may be evaluated in comparison to previous prediction parameter set scores 310.

At block 435, if a prediction parameter set 300 with a better prediction parameter set score 310 was found, the results of the prediction algorithm using the prediction parameter set 300 with the better prediction parameter set 310 score may be displayed.

At block 440, if a prediction parameter 300 set with a better prediction parameter set 310 score was not found, prediction parameter sets 300 may be combined through a crossover function using a probability rate. The probability rate may be used to select the type and location of the crossover. The probability rate may be set by the method, through experience or by a user. The crossover rate may be adjusted to create mutated prediction parameters 300.

At block 445, mutated prediction parameter 300 sets may be created. The prediction parameter 300 sets may be mutated given the probability rate. The probability rate may be used to select the type of mutation. The probability rate may be set by the method, through experience or by a user. The mutation rate of the prediction parameters 300 may be adjusted or applied to create mutated prediction parameters 300.

At block 450, the user may be permitted to stop the iterations submit the additional parameters 300. In some situations, the user may want to add input to the process. For example, the user may know that a particular adjustment may greatly speed up the process. The method may be stopped and a user may be permitted to submit the additional parameters 300.

At block 455, current prediction parameter 300 sets may be replaced with the mutated (either automatically or by the user) prediction parameter 300 sets. By adjusting the current prediction parameter 300 sets with the mutated prediction parameter 300 sets, new predictions may be made and evaluated.

At block 460, it may be determined whether the prediction parameter set 310 score has remained stable. In some embodiments, the determination may be whether the prediction parameter set 310 score has stayed within a statistically consistent range. If the prediction parameter set score 310 is consistent, this may be an indication that additional changes will not produce better results and that the method may be complete. If the prediction parameter set score 310 is determined to be stable at block 460, the results of the prediction algorithm using the most recent prediction parameter 300 set may be displayed at block 465, and the method may end.

During execution and in some embodiments, in real-time, the progress of the method may be displayed on a display device 191, such as in FIG. 3. The display 191 also may indicate one or more prediction parameters 300 currently being varied. The display 191 may be on a monitor in communication with the computer 110.

At block 470, it may be determined whether the maximum iterations of the method have executed. In execution, the method and mutations may continue for a significant amount of time. By limiting the time, the desire may be that a majority of the optimal prediction parameters 300 will be obtained. If the maximum iterations of the method have occurred, the results of the prediction algorithm using the most recent prediction parameter 300 set may be displayed at block 465, such as in FIG. 4 and the method may end. In other embodiments, the best result (closest prediction) found so far may be displayed. If the maximum iterations have not occurred, the method may proceed to block 415 and repeat by evaluating additional prediction parameters 300.

Once the forecast is complete, the user can save the evolved parameters and reuse then for other predictions, avoiding re-evolving from scratch. Other functionalities may include applying the prediction such performing some a business analysis that uses the prediction, export the predicted data, etc.

To summarize, the method may be used to predict medical data using sophisticated prediction tools by simply making a selection. In the past, a fundamental necessity to use such tools required from the users a profound knowledge in fields like mathematics and statistics. Using the prediction method described herein, removes the burden from a user to manually create and refine a data prediction algorithm. The described method removes the need for knowledge of how to manipulate the prediction parameters 300 and determines the optimal prediction parameters 300 automatically. The method is especially helpful at analyzing medical data, such as predicting DNA sequences. Additional examples may include the prediction and monitoring of cell growth and disease dispersion, muscle stimulation patterns of arm\leg movements, and sleep medical signals. Other examples may be recognizing patterns of heart rate, and improving management of glucose levels. It should be noted that these examples are not intended to be used to identify key features or essential features of the claimed subject matter, nor are intended to be used to limit the scope of the claimed subject matter.

Although the foregoing text sets forth a detailed description of numerous different embodiments of the invention, it should be understood that the scope of the invention is defined by the words of the claims set forth at the end of this patent. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of the claims defining the invention.

Thus, many modifications and variations may be made in the techniques and structures described and illustrated herein without departing from the spirit and scope of the present invention. Accordingly, it should be understood that the methods and apparatus described herein are illustrative only and are not limiting upon the scope of the invention.

The invention claimed is:

1. A computer implemented method of using genetic algorithms to create predictions of data comprising:
   loading data to be used for forecasting;
   dividing the data into a plurality of sections;
   creating prediction data using prediction parameters comprising;
      executing a prediction algorithm using the prediction parameters to create the prediction data;
      using one of the sections of the data, creating a prediction evaluation that indicates an accuracy of the prediction algorithm by comparing the created prediction data from the prediction algorithm to actual data in the one of the sections;
   determining if the prediction evaluation is above a threshold including:
      observing results of the created prediction evaluation and previous prediction evaluations;
      determining if the result of the created prediction evaluation continues to improve over the previous prediction evaluations;
      in response to the result of the created prediction evaluation continuing to improve over the previous prediction evaluations, increasing the threshold until a rate of improvement of the result of the created prediction evaluation slows; and
      in response to the result of the created prediction evaluation having not improved over the previous prediction evaluations over a preset number of iterations, lowering the threshold;
   when the prediction evaluation is above the threshold, reporting prediction evaluation results;
   when the prediction evaluation is below the threshold;
      creating additional prediction parameters by generating a plurality of copies of the prediction parameters and introducing random changes during the copying operation; and/or by allowing a user to submit the additional prediction parameters and substituting the additional prediction parameters for the prediction parameters; and
      repeating the creating the prediction data and determining when the prediction evaluation is above the threshold for a desired time or until the prediction evaluation is above the threshold.

2. The method of claim 1, wherein an initial set of prediction parameters is created using a random function.

3. The method of claim 1, wherein creating additional prediction parameters comprises creating a representation of values to be assigned to at least one of a plurality of prediction parameters used by the prediction algorithm.

4. The method of claim 1, wherein the prediction evaluation is created using a statistical analysis of the prediction data in comparison to the actual data.

5. The method of claim 1, further comprising:
   storing the prediction evaluation along with the prediction parameters;
   selecting the prediction evaluation and the prediction parameters that are optimal.

6. The method of claim 1, wherein creating additional parameters comprises at least one selected from a group comprising:
   adjusting a crossover rate of the prediction parameters; and
   applying a mutation rate of the prediction parameters created at design time of the method.

7. The method of claim 1, wherein the prediction parameters comprise prediction parameters and data parameters and prediction parameters comprise at least one selected from a group comprising:
   periodicity;
   complexity penalty;
   forecast method;
   historic model count
   historic model gap;
   instability sensitivity;
   maximum series value;
   minimum series value;
   minimum support;
   missing value substitution;
   periodicity hint;
   prediction smoothing; and
   wherein the data parameters comprise at least one selected from a group comprising:
   time series length; and
   time series density.

8. The method of claim 1, wherein the predictions are used for analysis of medical related data.

9. The method of claim 1, further comprising displaying progress of the method on a display in real-time comprising displaying a graph of the prediction data and a graph of the actual data wherein real-time is substantially as quickly as the predictions are created.

10. The method of claim 9, wherein a current value of all of the prediction parameters is displayed in real-time.

11. The method of claim 1, further comprising using a first section to train the method and a second section to validate the method.

12. The method of claim 11, further comprising rotating the sections until all the sections have both been used to train the method and to validate the method.

13. A computer implemented method of using genetic algorithms to create predictions of medical data comprising:
   loading data in a computer memory to be used for forecasting;
   opening a forecasting tool;
   generating multiple sets of prediction parameters randomly;
   evaluating prediction parameters sets comprising:
      using a prediction algorithm, creating a prediction with each of the prediction parameter sets;
      calculating a prediction parameter set score for each of the prediction parameter sets, wherein the parameter set score indicates an accuracy of the prediction algorithm using the prediction parameters;
   determining whether a better prediction parameter set was found comprising:
      observing the calculated prediction parameter set scores and previous prediction parameter set scores;
      determining if the calculated prediction parameter set scores continues to improve over the previous prediction parameter set scores;
      in response to the calculated prediction parameter set scores continuing to improve over the previous prediction parameter set scores, increasing an accuracy threshold until a rate of improvement of the calculated prediction parameter set scores slows; and in response to the calculated prediction parameter set scores having not improved over the previous prediction parameter set scores over a preset number of iterations, lowering the accuracy threshold;

comparing the calculated prediction parameter set scores with the accuracy threshold;

when the calculated prediction parameter set scores is above the accuracy threshold, displaying prediction algorithm results using the prediction parameter set with the calculated prediction parameter set score;

else, combining the prediction parameter sets through a crossover function using a probability rate;

creating mutated prediction parameter sets based on the prediction parameter sets comprising mutating the prediction parameter sets based on the probability rate;

allowing a user to submit the mutated parameter sets;

replacing current prediction parameter sets with the mutated prediction parameter sets;

determining whether the prediction parameter set score has remained stable comprising determining whether the prediction parameter set score has stayed within a statistically consistent range;

when the prediction parameter set score is determined to be stable, displaying the prediction algorithm results using a most recent parameter set;

ending the method;

determining whether maximum iterations of the method have executed;

when the maximum iterations of the method have occurred, displaying the prediction algorithm results using the most recent parameter set;

ending the method;

when the maximum iterations of the method have not been reached or the prediction parameter set score is not stable;

repeating the method starting at the evaluating block.

14. The method of claim 13, wherein the prediction parameter set score is created using a statistical analysis of the prediction in comparison to the data.

15. The method of claim 13, wherein creating additional parameters comprises at least one selected from a group comprising:

adjusting a crossover rate of the prediction parameters; and applying a mutation rate of the prediction parameters created at design time of the method.

16. The method of claim 13, wherein the prediction parameters comprise prediction parameters and data parameters and prediction parameters comprise at least one selected from a group comprising prediction parameters:
periodicity;
complexity penalty;
forecast method;
historic model count
historic model gap;
instability sensitivity;
maximum series value;
minimum series value;
minimum support;
missing value substitution;
periodicity hint; and
prediction smoothing; and wherein the data parameters comprise at least one selected from a group comprising:
time series length; and
time series density.

17. The method of claim 13, where progress of the method also indicates one or more prediction factors currently being varied.

18. The method of claim 13, further comprising using a first section of data to train the method and a second section of data to validate the method.

19. The method of claim 18, further comprising rotating the sections until all the sections have both been used to train the method and to validate the method.

20. A computer system, comprising:

a processor and a memory coupled to the processor, wherein the memory containing instructions that when executed by the processor, causing the processor to perform:

loading data to be used for forecasting;

dividing the data into a plurality of sections;

creating prediction data using prediction parameters comprising;

executing a prediction algorithm using the prediction parameters to create the prediction data;

using one of the sections of the data, creating a prediction evaluation that indicates an accuracy of the prediction algorithm by comparing the created prediction data from the prediction algorithm to actual data in the one of the sections;

determining if the prediction evaluation is above a threshold including:

observing results of the created prediction evaluation and previous prediction evaluations;

determining if the result of the created prediction evaluation continues to improve over the previous prediction evaluations;

in response to the result of the created prediction evaluation continuing to improve over the previous prediction evaluations, increasing the threshold until a rate of improvement of the result of the created prediction evaluation slows; and in response to the result of the created prediction evaluation having not improved over the previous prediction evaluations over a preset number of iterations, lowering the threshold;

when the prediction evaluation is above the threshold, reporting prediction evaluation results;

when the prediction evaluation is below the threshold;

creating additional prediction parameters by generating a plurality of copies of the prediction parameters and introducing random changes during the copying operation; and/or by allowing a user to submit the additional prediction parameters and substituting the additional prediction parameters for the prediction parameters; and repeating the creating the prediction data and determining when the prediction evaluation is above the threshold for a desired time or until the prediction evaluation is above the threshold.

\* \* \* \* \*